(12) United States Patent
Hallbäck et al.

(10) Patent No.: US 8,371,298 B2
(45) Date of Patent: Feb. 12, 2013

(54) METHOD AND APPARATUS FOR LUNG VOLUME ESTIMATION

(75) Inventors: Magnus Hallbäck, Bromma (SE); Mario Loncar, Ekerö (SE); Pär Emtell, Vällingby (SE); Christer Ahlmén, Sollentuna (SE)

(73) Assignee: Maquet Critical Care AB, Solna (SE)

( * ) Notice: Subject to any disclaimer, the term of this patent is extended or adjusted under 35 U.S.C. 154(b) by 1183 days.

(21) Appl. No.: 12/095,825

(22) PCT Filed: Dec. 6, 2005

(86) PCT No.: PCT/EP2005/056529
§ 371 (c)(1),
(2), (4) Date: Jun. 2, 2008

(87) PCT Pub. No.: WO2007/065475
PCT Pub. Date: Jun. 14, 2007

(65) Prior Publication Data
US 2008/0289628 A1    Nov. 27, 2008

(51) Int. Cl.
*F16K 31/02* (2006.01)
(52) U.S. Cl. ......... 128/204.22; 128/204.23; 128/205.11; 128/205.15; 600/532; 600/538
(58) Field of Classification Search ............ 128/203.12, 128/205.11, 204.22, 205.15, 204.23, 200.26; 600/529, 532, 538
See application file for complete search history.

(56) References Cited

U.S. PATENT DOCUMENTS

| | | | |
|---|---|---|---|
| 4,941,476 A | 7/1990 | Fisher | |
| 6,010,459 A * | 1/2000 | Silkoff et al. | 600/532 |
| 6,139,506 A | 10/2000 | Heinonen | |
| 6,305,212 B1 | 10/2001 | Drzewiecki | |
| 6,413,226 B1 * | 7/2002 | Starr et al. | 600/532 |
| 7,367,954 B2 * | 5/2008 | Starr et al. | 600/532 |
| 7,465,275 B2 * | 12/2008 | Stenqvist | 600/532 |
| 2003/0013980 A1 * | 1/2003 | Starr et al. | 600/532 |
| 2005/0121033 A1 * | 6/2005 | Starr et al. | 128/204.18 |

* cited by examiner

FOREIGN PATENT DOCUMENTS
EP     1 510 232     3/2005

OTHER PUBLICATIONS

"Estimation of Functional Residual Capacity at the Bedside Using Standard Monitoring Equipment: A Modified Nitrogen Washout/Washin Technique Requiring a Small Change of the Inspired Oxygen Fraction," Olegård et al, Anesth. Analg., vol. 101 (2005) pp. 206-212.

*Primary Examiner* — Lynne Anderson
(74) *Attorney, Agent, or Firm* — Schiff Hardin LLP

(57) ABSTRACT

In a method, ventilator and ventilator control unit for determining an end-expertorial lung volume (EELV) for a mechanically ventilated patient, a breathing gas is provided to the patient that has a first fixed N2/O2 gas composition, at least until the N2/O2 gas composition in air expired from the patient is constant. At least once, at a first predetermined point in time, the N2/O2 gas composition in the breathing gas is changed to a second fixed composition. The change in the N2/O2 gas composition exhaled by the patient for each breath is measured until a second point in time at which the level of expired $O_2$ in at least two subsequent breadths is substantially stable. The measurement is made downstream of the expiratory tube of the ventilator. The total gas volume is determined for each breath, and the EELV of the patient's lungs is determined based on the change in $O_2$ level between the first and second points in time.

24 Claims, 4 Drawing Sheets

FIG. 6
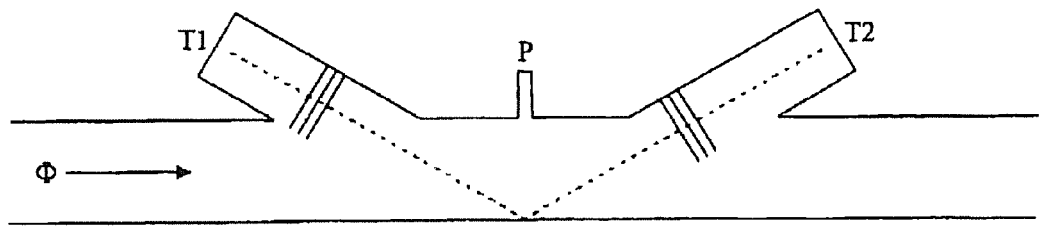
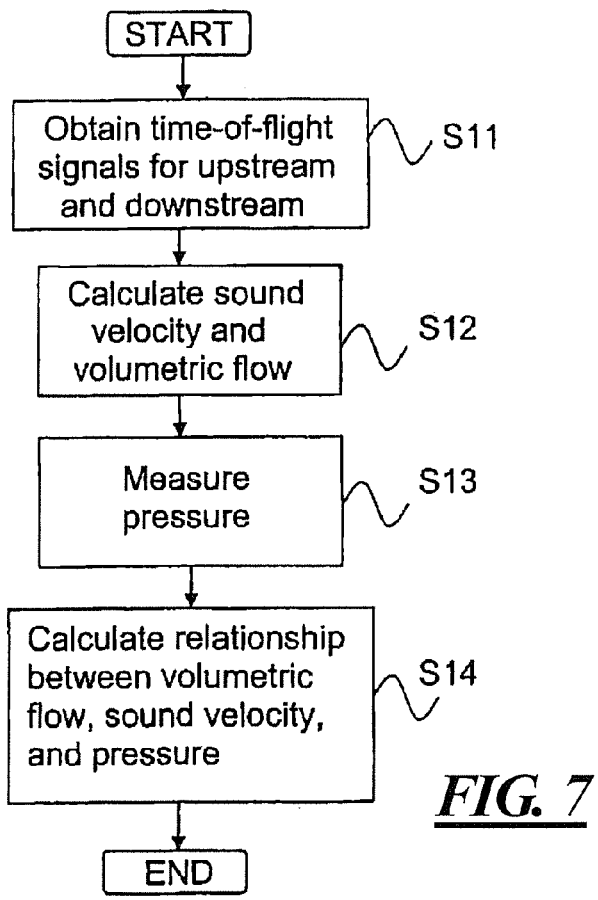
FIG. 7

METHOD AND APPARATUS FOR LUNG VOLUME ESTIMATION

BACKGROUND OF THE INVENTION

1. Field of the Invention

The present invention relates to a ventilator for the ventilation of a patient as well as a control unit therefrom and to a method for operating a ventilator.

2. Description of the Prior Art

The functional residual capacity (FRC) of a person is the volume of the lung after expiration at normal pressure. End-expiratory lung volume (EELV) is defined as the volume of gas that remains in the respiratory passages of a patient that is being mechanically ventilated, at the end of a normal expiration. In the case of an elevated positive end expiratory pressure (PEEP), that is, if the end expiratory pressure is higher than the normal pressure, the end expiratory lung volume will be greater than the functional residual capacity. For ZEEP (zero end expiratory pressure, that is, PEEP=0) FRC is equal to EELV.

From a clinical point of view the end-expiratory lung volume is useful, since an abnormally low value may indicate that a part of the lung has collapsed and does not participate in the gas exchange in the lung. Therefore, a simple way of determining the end-expiratory lung volume would be desired, to enable the study of a patient's development over time, for example by determining the end-expiratory lung volume measurement once an hour. Such measurements might also be carried out before and after attempts to open parts of the lung that have been collapsed, a so called lung recruitment maneuver. Thus, measurements of the end-expiratory lung volume could be a complement to other measurement values, such as arterial $O_2$ saturation, which provides valuable information about the ventilation of the patient.

In research applications the washout of an inert gas is used to determine the end-expiratory lung volume. It has been more difficult to find a method that is acceptable for clinical use.

Olegård et al.: "Estimation of Functional Residual Capacity at the Bedside Using Standard Monitoring Equipment: A Modified Nitrogen Washout/Washin Technique Requiring a Small Change of the Inspired Oxygen Fraction", Anesth Analg 2005; 101:206-12 discloses a method for estimating the FRC or EELV by means of nitrogen washout. Such a method can provide satisfactory results using changes of $O_2$ level in the breathing gas of approximately 10% and procedure duration of approximately 4 minutes, which has been found to be acceptable even in critically ill patients. In this article, the calculations are based on the difference in inspiratory $N_2$ concentration between the start and end of a washout procedure.

The use of $O_2$ or $N_2$ as an indicator gas is advantageous, since these gases are already available from the ventilator, and also are not harmful to the patient.

SUMMARY OF THE INVENTION

It is an object of the invention to enable a reliable method for determining the end-expiratory lung volume that is acceptable from a clinical point of view and that will provide a more accurate result than that described above.

This object is achieved by a ventilator for ventilation of a patient, including an inspiration gas circuit for providing breathing air, that is a mixture of N2 and $O_2$ to the patient and an exhalation gas circuit for receiving exhaled air from the patient and a gas outlet for the exhaled air. The ventilator has a control unit configured to calculate the end expiratory lung volume, EELV, of a patient being ventilated by the ventilator, based on the expired volume per breathing cycle and the difference between the $N2/O_2$ composition in the expired gas at a first point in time and a second point in time. The control unit is further configured to calculate, for each breath between the first and second points in time, the difference in the N2/O2 composition exhaled and the amount of N2 and/or O2 exhaled just after the second point in time. The ventilator also has a measuring unit for measuring the level of O2 in the expired gas, the measuring unit being arranged near the gas outlet.

The object is also achieved by a method of determining an end-expiratory lung volume, EELV, for a mechanically ventilated patient, where a breathing gas is provided to the patient through an inspiratory tube and removed from the patient through an expiratory tube, including the following steps:

providing a breathing gas having a first fixed N2/O2 gas composition to the patient at least until the N2/O2 gas composition in air expired from the patient is constant, changing, at least once, at a determined first point in time, the N2/O2 gas composition to a second fixed composition in the breathing gas, measuring the change in N2/O2 gas composition exhaled by the patient for each breath until a second point in time at which the level of expired O2 in at least two subsequent breaths is substantially stable, the measurement being made downstream of the expiratory tube determining the total gas volume of each breath, determining the EELV of the patient's lungs based on the change in $O_2$ level between the first and second points in time.

If the gas composition is measured downstream of the expiratory tube the measured indicator gas (O2 or N2) will include only the expired indicator gas. When performing measurements at the Y piece, as is common in the art the O2 or N2 level will vary very fast since the measured gas will change between breathing gas and expired gas. Thus, to provide reliable measurements of the O2 or N2 level at this point a very fast sensor would be needed. By measuring at the outlet the expiration gas will be mixed in the second tube, that is, the tube carrying expired gas from the patient, so that the fraction of $O_2$ in the expiration gas will vary more smoothly. Thus the measurement can be carried out in a reliable way even using a sensor that is not so fast.

In one embodiment the control unit calculates the EELV according to $$EELV = \frac{\sum_{n=1}^{N} VCe_n \cdot (x_n - x_{after})}{x_{before} - x_{after}} - V_{system}$$

where $VCe_n$ is the volume of expired gas at breath number n between the first and second points in time, $V_{system}$ is the volume contained in the ventilator and patient tubing system from the gas delivery valves to the gas analyser point on the expiratory side x is a quantity that varies linearly with the expired N2/O2 composition, and $x_n$ is the value of the quantity in breath number n between the first and second points in time, $x_{before}$ is the value of the quantity before the first point in time, $x_{after}$ is the value of the quantity at or just after the second point in time.

For example, x may be the density of the gas, p, the concentration of O2 or N2 in the gas, the viscosity, the thermal conductivity, or any other quantity that varies linearly with the mixed expired N2/O2 composition.

For the density of the gas, the equation above becomes $$EELV = \frac{\sum_{n=1}^{N} VCe_n \cdot (\rho_n - \rho_{after})}{\rho_{before} - \rho_{after}} - V_{system}$$

where $\rho_n$ is the density of the gas in each breath between the first and second points in time, $\rho_{before}$ is the density of the gas before the first point in time, $\rho_{after}$ is the density of the gas at or just after the second point in time.

The control unit may be arranged to calculate the end expiratory lung volume, EELV, according to $$EELV = \frac{\sum_{n=1}^{N} VCe_n \cdot (O2mix_n - O2mix_{after})}{O2mix_{before} - O2mix_{after}} - V_{system}$$

where $VCe_n$ is the volume of expired gas at breath number n between the first and second points in time, $O2mix_n$ is the level of $O_2$ in the mixed expired gas at breath number n between the first and second points in time, $O2mix_{after}$ is the level of O2 in the mixed expired gas at a breath just after the second point in time and $O2mix_{before}$ is the level of $O_2$ in the mixed expired gas at a breath at the first point in time.

Preferably, the control unit is arranged to correct the values $\rho_n$, $\rho_{before}$ and $\rho_{after}$ for temperature before calculating the EELV, to eliminate the risk of a temperature induced drift that may disturb the proportionality between density ρ and the gas composition.

According to a preferred embodiment the control unit further comprises control means for controlling the O2 level in the breathing gas supplied from the ventilator to the patient in such a way as to change the O2 level in the breathing gas at the first point in time.

The ventilator may also include a measuring unit for measuring the volume flow of expired gas, the measuring unit preferably being arranged near the gas outlet.

In one preferred embodiment the measuring means comprises an ultrasound sensor arranged to provide data related to the gas flow to the control unit.

If ultrasound measurements are used to determine both the volumetric and the mass gas flow, no separate gas concentration sensor is needed. There is no need to determine the actual gas concentrations; a parameter that varies linearly with the gas concentration of O2 or N2 can be used. Such a parameter is the density, or any other parameter that is proportional to the density. Thus, if the ultrasound sensor is used for determining the volumetric flow and the mass flow, no separate $O_2$ sensor or N2 sensor is needed.

The step of changing the N2/O2 composition preferably involves increasing the level of O2. The first composition may have more or less O2 than a normal N2/O2 air composition provided to the patient.

The step of changing the level of O2 typically involves changing the level of O2 by a unit of 5%-30% of the total volume, for example by a unit of 10%.

The step of determining the total gas volume of each breath is preferably performed by a volume sensor downstream of the expiratory tube.

The invention also relates to a control unit for a ventilator as defined above.

BRIEF DESCRIPTION OF THE DRAWINGS

FIG. 6 shows, schematically, an arrangement for measuring the gas flow in a channel, known per se.

FIG. 7 is an overall flow chart of a method that may be used to determine the mass flow according to a preferred embodiment of the invention.

DESCRIPTION OF THE PREFERRED EMBODIMENTS

Figure 1:
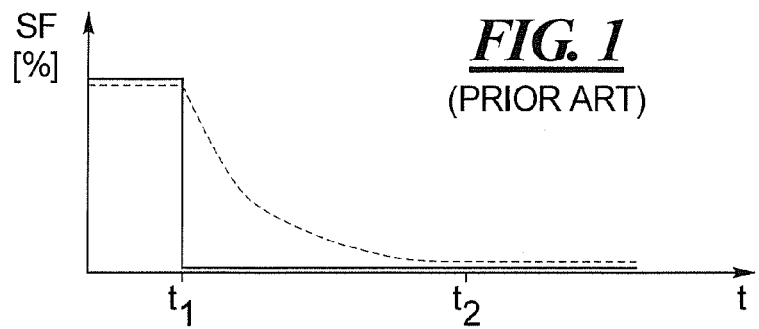
FIG. 1 is a diagram of the washout of an indicator gas such as SF6 from a patient's lungs.

FIG. 1 illustrates the principle of gas washout according to the prior art. A certain amount of an inert gas, such as SF6, is added to the breathing gas. The solid line illustrates the fraction of SF6 in the breathing gas that is inspired by the patient. The dashed line illustrates the fraction of SF6 in the expiration gas. The patient is ventilated with the SF6 containing gas until the fraction of SF6 in the patient's lungs reaches a predetermined level, for example, 2%. The total volume of SF6 in the patient's lungs is then $VSF_6 = V_{lung} * F_{SF6}$, where $V_{lung}$ is the patient's lung volume and FSF6 is the fraction of SF6, that is, 2% in this example. Thus, the total lung volume is $V_{lung} = V_{SF6}/F_{SF6}$.

As can be seen in FIG. 1, when the SF6 is removed from the inspiration gas at $t_1$, the level of SF6 in the expiration gas will drop asymptotically towards zero. The total amount of SF6 in the patient's lungs can be determined by measuring the total amount of SF6 that is exhaled by the patient until a point $t_2$, at which there is no more SF6 in the expiration gas.

The volume of expired SF6 can be expressed as $$V_{SF6} = \int \Phi_{exp}(t) \cdot F_{SF6}(t) dt \qquad (1)$$

According to the invention and as is known in the prior art, instead of adding a gas and determining the total volume of this gas, one of the gases present in the breathing gas, that is, $O_2$ or $N_2$, can be used as an indicator gas instead. At a defined point in time the level of $O_2$ or $N_2$, respectively, is then lowered and the washout of this gas is monitored. To minimize any negative effects for the patient, the level of $O_2$ is preferably increased for a period of time before it is reduced. The increase, and reduction, may be performed, for example, in steps of 10%.

While the description is based on measurements of $O_2$, the skilled person is well aware that the $N_2$ level, or the combined level of $O_2$ and $N_2$, could be measured instead. The skilled person is aware of how to measure the level of these different gases. Since the levels of O2 and N2 depend on each other, either level can be used in the calculations.

Figure 2A:
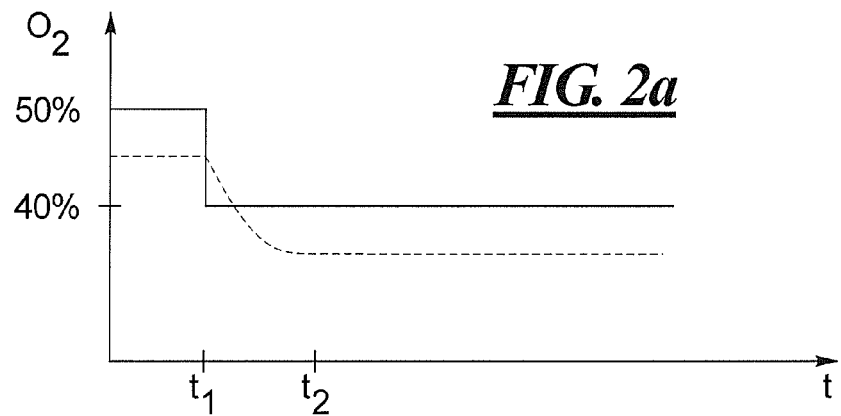
FIG. 2a is a diagram of the washout of O2 from a patient's lungs if the amount of O2 is reduced in the breathing gas.

FIG. 2a is a diagram using $O_2$ as an example and illustrating the level of $O_2$ in the breathing gas and in the expired gas as a function of time. In this example, the breathing gas comprises 50% oxygen. The expired gas comprises 45% oxygen. At time $t_1$ the $O_2$ level of the breathing gas is lowered to 40%. The $O_2$ level in the expired gas will then decrease gradually until a new stable value of $O_2$ is reached. This is referred to as a partial washout of $O_2$. FIG. 2a illustrates the basic principle for washout, which may be used, for example, when a test person is connected to the ventilator for a brief period of time and for the sole purpose of determining the EELV. If a patient is being ventilated by the ventilator, a change in the O2 level should normally only be temporary, as shown in FIG. 2b.

Figure 2B:
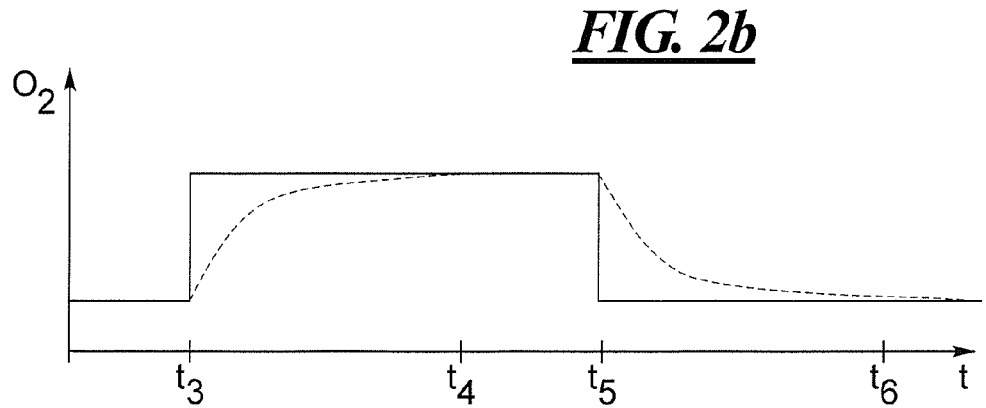
FIG. 2b is a diagram of the change of O2 level in a patient's lungs following a first and a second change in the O2 level of the breathing gas.

FIG. 2b is a diagram showing the preferred situation where a first change in the O2 level is made at a first point in time t3. At a second point in time t4 the O2 level in the expiration gas is stable again. A second change back to the original level is made at a third point in time t5. At a fourth point in time the O2 level in the expiration gas is stable again after the second change. The procedure indicated in FIG. 2b is the normal one when a patient is connected to the ventilator for ventilation. The O2 level in the breathing gas is indicated as a solid line and the O2 level in the expiration gas is indicated as a dashed line. The first change is preferably an increase of the O2 level, to ensure sufficient O2 to the patient. If the O2 level is so high that an increase is not feasible, the first change may instead be a reduction of the O2 level.

In this way, two EELV values can be obtained: one after the first change of O2 level and one after the second change.

The step of changing the level of O2 typically involves changing the level of O2 by a unit of 5%-30% of the total volume, for example by a unit of 10%. The levels proposed in this document have been found to be acceptable from a clinical point of view. It should be noted that too high O2 levels may result in oxygen poisoning for longer periods of exposure.

The EELV may be obtained regularly, for example at regular time intervals set by the operator adapted to the condition of an individual patient. The monitoring may be supplemented by an alarm issued automatically, for example, if the EELV drops below a specified threshold value.

Figure 3:
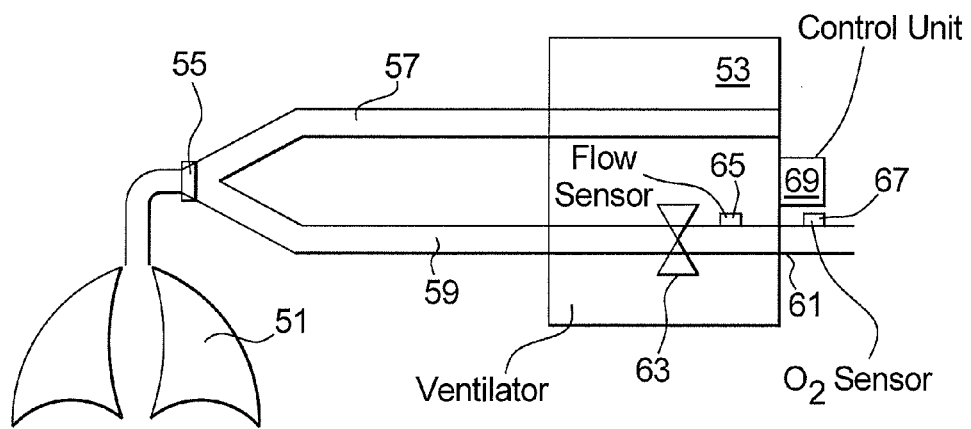
FIG. 3 illustrates a measurement arrangement for measuring the washout of O2 according to a first embodiment of the invention.

FIG. 3 illustrates the ventilation of a patient, represented by a pair of lungs 51. The patient is ventilated using a ventilator 53 which is connected to the patient through a Y piece 55 which interconnects a first tube 57 for breathing gas provided by the ventilator and a second tube 59 for removing expired air from the patient, with the patient's lungs in the way common in the art. As is well known, the breathing gas will normally comprise an appropriate mixture of air and O2. The expired air is output to the surroundings from the ventilator at a gas outlet 61, for example through a valve 63. Usually, the measurements of $CO_2$, $O_2$ and gas flow are performed at the Y piece 55. The gas flow at the Y piece alternates between inspiration gas and expiration gas, which means that the O2 content varies very quickly since the flow changes direction for each breath. According to the invention, instead, the $O_2$ measurements are performed at the gas outlet, where the variations in the gas composition are smoother since only expiration gas is measured.

In this way, the expiration gas will be mixed in the second tube 59 so that the fraction of $O_2$ in the expiration gas will vary more smoothly, making it easier to measure in a reliable way.

It would also be possible to use a ventilator provided with a very large mixing chamber and a mechanical stirring means for mixing the gas, as is known in the prior art. In this case, a very slow O2 sensor would be acceptable. Preferably, according to the invention, the tubes already present in the ventilator are used without any additional chamber.

The gas flow too may be measured at the gas outlet 61 or the valve 63. This is advantageous since measuring the flow and the fraction of $O_2$ at the same or practically the same point will lead to a more reliable result. As shown in FIG. 3, a flow sensor 65 is provided near the valve 63, upstream or downstream of the valve 63, and an O2 sensor 67 is provided near the gas outlet 61. The ventilator itself, as well as the flow sensor 65 and the O2 sensor 67 are controlled by one or more control units, which are represented in FIG. 3 by one control unit 69. The sensors 65, 67 as well as the control unit 69 may be located externally or may be integral parts of the ventilator 53. In FIG. 3, the control unit 69 is also used for performing the calculations discussed below. These calculations may of course be performed in a separate calculation unit of the ventilator, or in an external unit.

When the measurements are performed at or near the outlet 61 from the ventilator, the total volume of the ventilation system, that is, the patient's respiratory passages as well as the tubes and the ventilator itself, must be taken into account in the calculations. The volume of the ventilator system must be subtracted from the result to obtain the EELV.

Figure 4:
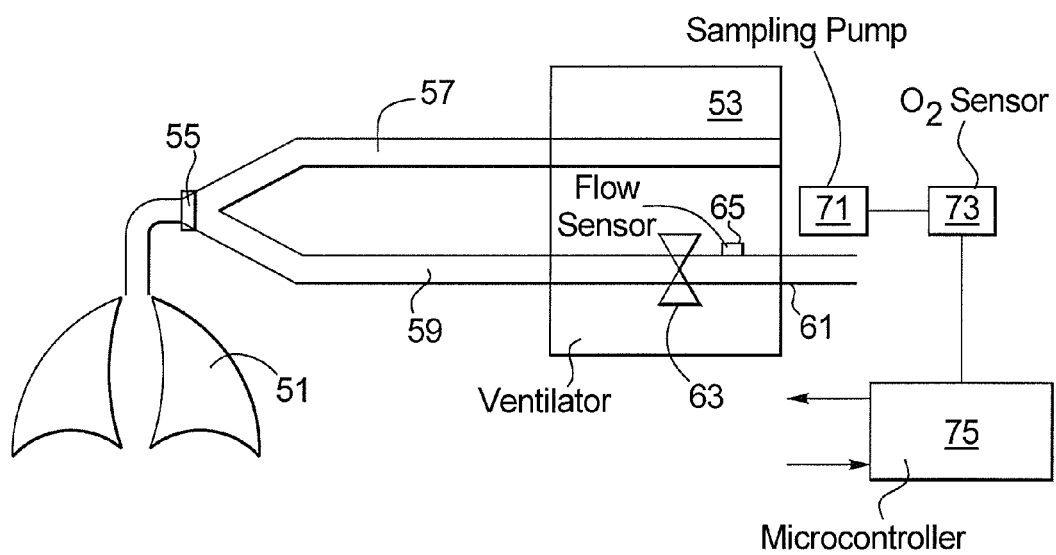
FIG. 4 illustrates a measurement arrangement for measuring the washout of O2 according to a second embodiment of the invention.

FIG. 4 illustrates a ventilator and measurement apparatus slightly different from the one shown in FIG. 3. The lungs 51, ventilator 53, Y piece 55, inspiratory and expiratory tubes 57, 59, outlet 61, valve 63 and flow sensor 65 are essentially as discussed in connection with FIG. 3. In contrast to that shown in FIG. 3, the gas composition is determined in a sidestream to the expiratory tube 59. In the embodiment shown in FIG. 4, a sampling pump 71 is arranged in the sidestream for sampling the gas flow at the outlet. An O2 sensor 73 receives gas samples from the sampling pump 71 and determines the gas composition, in particular the O2 or N2 content of the gas. The measurement results from the O2 sensor 73, and from the flow sensor 65, are fed to a microcontroller 75, which performs the calculations according to the invention. Alternatively, the microcontroller 75 is arranged for communication with an external computer, for example, through a USB interface and for communication with the ventilator for controlling the function of the ventilator. The necessary calculations according to the invention may then be performed in the external computer.

According to the invention the algorithms used for flow and concentration measurements are based on the following.

This algorithm requires a very stable composition of the breathing gas. This means that the inspiration part of the ventilator must be very reliable. A constant error in the composition will be acceptable but the composition should ideally not vary at all. Also, the patient's O2 absorption is assumed to be constant throughout the measurement period. Experiments have indicated that this is the case to the extent needed to provide reliable measurements.

The assumption is made that the change in O2 level after completed washout is the same, $\Delta FO2$, in all parts of the lung and in all other parts of the system (F denotes volume fraction of a gas component, in this case O2). If this is the case, the amount of O2 must be the difference in supplied and expelled O2 during the washout, as given in Eq (2).

$$(EELV + V_{system}) \cdot \Delta FO2 = VO2out - VO2in \qquad (2)$$

Here, $\Delta FO2 = FO2_{before} - FO2_{after}$. VO2out (unit Litre or $m^3$) is measured on the expiration side. For each breathing cycle the outflow volume of O2 through the valve 63 is measured. VCeO2 is defined by Eq. (3) as the volume of expired O2 per cycle (unit Litre or m³):

$$VCeO2_n = \int_{t_n}^{t_n+\Delta t} \dot{V}e(t) \cdot FO2(t) dt \tag{3}$$

FO2(t) is the fraction of O2 measured at the outlet 61. VO2out is the sum of the $VCeO2_n$ for all cycles during the washout.

The parameter VCe, represents the volume per cycle of expired gas as given by Eq. (4):

$$VCe_n = \int_{t_n}^{t_n+\Delta t} \dot{V}e(t) dt \tag{4}$$

$\dot{V}e(t)$ is the flow measured by the expiration flow sensor given a defined reference state, for example, AP21 (i.e. ambient barometric pressure and 21° C.).

Thus, VCe and VCeO2 are given as volumes for a particular reference state, for example, AP21.

VO2in, that is the net supply of O2 to the gas volume, comprises two parts:
1. a positive contribution from the inflow of O2 on the inspiration side, and
2. a negative contribution from the patient's oxygen absorption.

It is assumed that VO2in can be obtained as a sum, for all breaths, of the mean inflow of O2 per breath, $\overline{VCiO2}$.

VO2out during washout is the sum of the cycle volumes $VCeO2_n$. Eq. (2) can then be rewritten as:

$$(EELV + V_{system}) = \frac{1}{\Delta FO2} \sum_{n=1}^{N} (VCeO2_n - \overline{VCiO2}) \tag{5}$$

After the valves in the inspiration part of the system have been adjusted to the new O2 level during the washout phase, VCiO2 is assumed to be constant. When the washout is completed and the O2 level of the system has reached the new equilibrium, VCiO2 equals VCeO2. Hence, VCiO2 can be determined from VCeO2 after the washout:

$$\overline{VCiO2} = VCeO2_{after} \tag{6}$$

Equation (5) may be rewritten as:

$$(EELV + V_{system}) = \frac{1}{\Delta FO2} \sum_{n=1}^{N} (VCeO2_n - VCeO2_{after}) \tag{7}$$

$VCeO2_n$ varies with the breath volume, which can vary to a certain extent even when mechanically ventilating a patient. To obtain a value that will have smaller fluctuations the standardized value O2mix is defined as the concentration of O2 expelled during each breath:

$$O2mix_n = \frac{VCeO2_n}{VCe_n} \tag{8}$$

Inserting O2mix in equation (7) yields:

$$(EELV + V_{system}) = \frac{1}{\Delta FO2} \sum_{n=1}^{N} \left( \begin{array}{c} VCe_n \cdot O2mix_n - \\ VCe_{after} \cdot O2mix_{after} \end{array} \right) \tag{9}$$

Finally it is assumed that the mean expired gas volume for each cycle is the same during and after the washout. In this way a more reliable value of $VCe_{after}$ can be obtained, based on several breaths measured during and after the washout.

$$\frac{1}{N} \sum_{n=1}^{N} VCe_n = VCe_{after} \tag{10}$$

Eliminating $VCe_{after}$ from Eq. (9) finally yields an equation that can be used to determine the end-expiratory lung volume, EELV:

$$(EELV + V_{system}) = \frac{1}{\Delta FO2} \sum_{n=1}^{N} VCe_n \cdot (O2mix_n - O2mix_{after}) \tag{11}$$

The change in the O2 level in the volume, $\Delta FO2 = O2mix_{before} - O2mix_{after}$, may be determined from the difference of $O_2$mix between the states before and after the washout. $O2mix_{after}$ may be determined as a mean value over a number of breaths, for example ten, after the washout is considered to be completed.

In summary, end-expiratory lung volume, EELV can be calculated using Eq. (12):

$$EELV = \frac{\sum_{n=1}^{N} VCe_n \cdot (O2mix_n - O2mix_{after})}{O2mix_{before} - O2mix_{after}} - V_{system} \tag{12}$$

O2mix is determined from Eq. (13)

$$O2mix_n = \frac{VCeO2_n}{VCe_n} \tag{13}$$

The expired volumes per breathing cycle is obtained from the integrals of Equations (14) and (15):

$$VCeO2_n = \int_{t_n}^{t_n+\Delta t} \dot{V}e(t) \cdot FO2(t) dt \tag{14}$$

$$VCe_n = \int_{t_n}^{t_n+\Delta t} \dot{V}e(t) dt \tag{15}$$

Where $\dot{V}e(t)$ is the flow measured by the expiration flow sensor given for a particular reference state, such as AP21. It should be noted that $\dot{V}e(t)$ includes the bias flow, in the case where there is a bias flow superimposed on the expiratory flow.

If the system volume, $V_{system}$, is unknown it can be determined through pressurizing the tubes to a certain level (for example 50 cmH2O) and measuring the amount of supplied gas—in a similar way to that used for pre-use check procedure in the Maquet Servo-i ventilator.

The measured O2 level mirrors the change in N2 since it is assumed that the other gases present in expired air are not affected by the measurements. Thus, the O2 level or N2 level may be measured, depending on what is found to be the easiest.

The volumetric flow may be measured using any type of flow sensors known in the art, including:
 differential pressure flow sensors
 thermal flow sensors
 vortex shedding sensors
 ultrasonic sensors The gas concentration or composition may be measured using any type of O2 or N2 sensors known in the art, including:
 electro-chemical sensors
 paramagnetic sensors
 laser diode sensors
 sensors based on fluorescence Those skilled in the art are familiar with these and several other types of sensors that may be used according to the invention.

When using the method of FIGS. 6 and 7, or any $O_2$ concentration measurement procedure, in the context of FIGS. 3 and 4, since the quotient between variations in concentration is used, the O2 or N2 sensor does not have to be calibrated with respect to offset. It is sufficient that the sensor has a linear characteristic compared to the actual concentration.

Instead of the density of the gas composition, or the concentration of O2 or N2 in the gas, as discussed above, any quantity that varies linearly with the mixed expired N2/O2 composition can be used. Such quantities are, for example, the density, the viscosity and the thermal conductivity of the gas. Thus, a generalized expression of equation 12 above becomes $$EELV = \frac{\sum_{n=1}^{N} VCe_n \cdot (x_n - x_{after})}{x_{before} - x_{after}} - V_{system} \quad (16)$$

where x is a quantity that varies linearly with the expired N2/O2 composition, and $x_n$ is the value of the quantity at breath number n between $t_1$ and $t_2$, $x_{before}$ is the value of the quantity at $t_1$, $x_{after}$ is the value of the quantity at or just after $t_2$.

Hence, in the general case, the O2 concentration sensor 67 of FIG. 4 could be any kind of sensor measuring a quantity that varies linearly with the N2/O2 composition.

The gas flow and indirect concentration measurements according to this second aspect of the invention may be performed by any means known in the art. It is particularly advantageous, however, to use the method discussed in connection with FIGS. 6 and 7 below. If the ultrasound sensors are used to obtain both the volumetric flow of gas, as is common in the art, and the mass flow, as proposed above, only one set of sensors is needed to determine both the flow and the fraction of $O_2$, or the change in the fraction of $O_2$ in the total gas. The separate $O_2$ sensor that would otherwise be required can then be eliminated. The sensors 65 and 67 can be implemented as one sensor.

Since only a concentration quantity is needed that is linearly proportional to the true gas concentration for the method to work, the concentrations for $O2mix_n$, $O2mix_{before}$ and $O2mix_{after}$ in equations 9, 11 and 12 can be replaced by the densities $\rho_n$, $\rho_{before}$, $\rho_{after}$, so that, for example, equation 12 becomes $$EELV = \frac{\sum_{n=1}^{N} VCe_n \cdot (\rho_n - \rho_{after})}{\rho_{before} - \rho_{after}} - V_{system} \quad (17)$$

where $\rho_n$ is the density of the gas at breath number n between $t_1$ and $t_2$, (see FIG. 2 for $t_1$ and $t_2$)

$\rho_{before}$ is the density of the gas at $t_1$, $\rho_{after}$ is the density of the gas at or just after $t_2$.

To eliminate the risk of a temperature induced drift of the density variable, the measurement setup should be complemented by a temperature sensor, which may be slow since its primary role is to remove any bias due to slow temperature drift during the EELV measurement procedure. To clarify, for the density to be a proportional quantity to the gas concentration, the density has to be recalculated from the actual temperature to a reference ditto.

Figure 5:
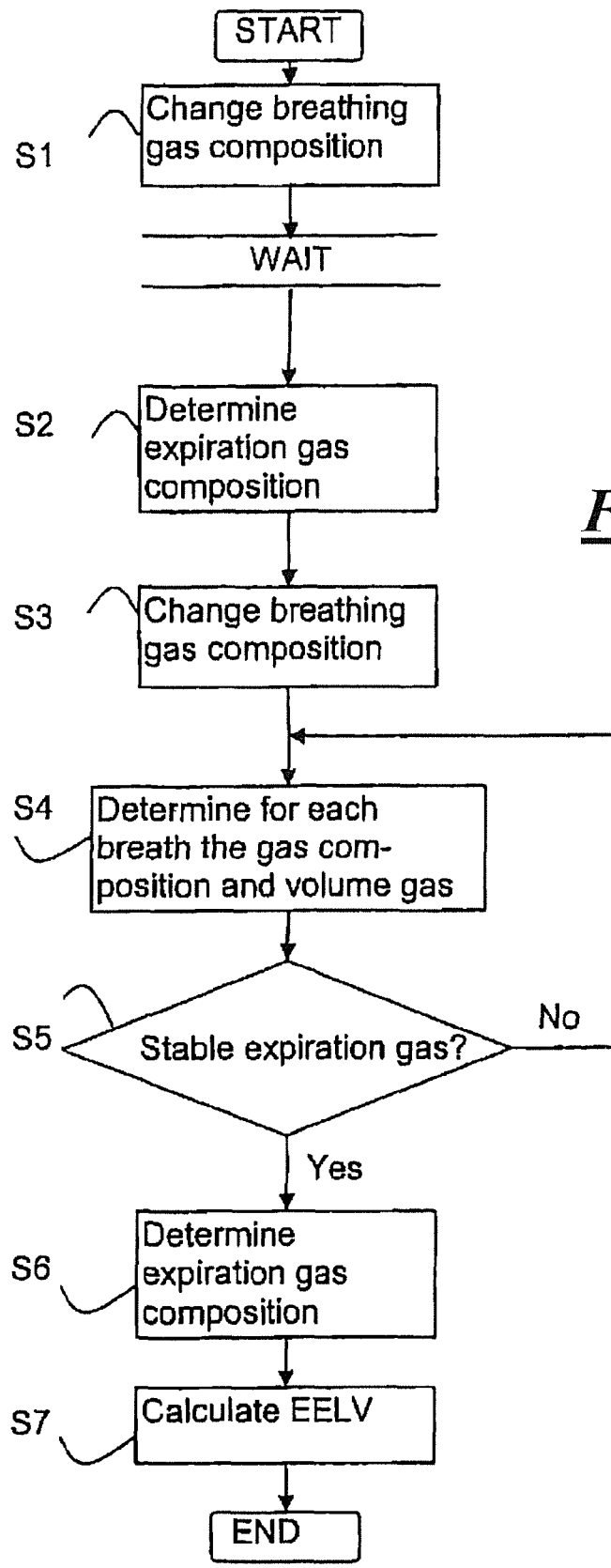
FIG. 5 is an overall flow chart of the inventive method.

FIG. 5 is an overall flowchart of the inventive method.

In an optional step S1, the composition of the breathing gas, that is, in particular the O2 level or N2 level, is changed.

When the composition of the expiration gas has stabilized after the change, or if no change is made, the composition of the expired gas is determined, in step S2.

In step S3: the composition of the breathing gas is changed again. If the O2 level was increased in step S1, it is reduced in step S3. If the O2 level was reduced in step S1, it is increased in step S3.

In step S4, the gas composition and volume in the expired gas is determined for each breath.

In step S5 it is determined whether the gas composition in the expired gas has stabilized after the change performed in step S3. If no: go to step S4; if yes, go to step S6.

Step S6: Determine the gas composition of the expiration gas after the gas composition has stabilized again.

Step S7: Determine the EELV based on the gas composition before, during and after the washout (or washin) and the gas volume for each breath. This may be done, for example, by means of equations 12, 16 or 17.

Step S1 is an optional step that may be performed to avoid negative effects on the patient from changing the gas composition. It does not have to be performed if the breathing gas composition can be changed for the EELV determination without affecting the patient negatively, or if the patient is only being ventilated only to determine the EELV, so that the ventilation starts at step S2.

If step S1 is performed, that is, an initial change of the breathing gas composition is made, an EELV measurement may also, or alternatively, be performed during the washin or washout that takes place between steps S2 and S3. To do this, the steps S4 to S7 are performed between steps S2 and S3, instead of, or in addition to being performed after step S3.

It will be advantageous to obtain two EELV values: one after the first change of breathing gas composition and one after the second change of breathing gas composition. In this way a more reliable value can be obtained.

The density can be determined by means of an ultrasound sensor, as will be discussed in the following.

In FIG. 6, a gas flow $\Phi$ passes through a gas flow channel. A first and a second ultrasound transducer, T1, resp. T2, are arranged to measure the gas flow in the channel, according to the prior art. A pressure sensor P is also included. As is common in the art, both transducers T1, T2 act as both transmitter and receiver. A pulse train is transmitted from the first transducer T1 and received by the second transducer T2, that is, in essentially the same direction as the gas flow. The time of flight downstream $tof_{do}$ is measured. Then a pulse train is transmitted in the opposite direction, from T2 to T1, and the time of flight upstream $tof_{up}$ is measured. The time of flight upstream and the time of flight downstream will differ and can be used to indicate the gas flow volume. Those skilled in the art familiar with such methods. The relative positions of the transducers T1, T2, and the pressure sensor P, can be varied, as is well known in the art.

According to the invention, the time of flight values $tof_{up}$ and $tof_{do}$ can be used, together with the pressure value, to determine the mass flow of gas, according to the following:

The time of flight signals obtained from the ultrasound transducers are used to calculate two values:

1) $\Phi_{actual}$, which is proportional to the flow velocity, and thus to the volumetric flow at a particular state of the gas:

$$\Phi_{actual} = k_1 \cdot \frac{tof_{up} - tof_{do}}{tof_{up} \cdot tof_{do}} \quad (18)$$

2) $c_{actual}$, which is proportional to the velocity of sound in the gas:

$$c_{actual} = k_2 \cdot \frac{tof_{up} + tof_{do}}{tof_{up} \cdot tof_{do}} \quad (19)$$

In equations (18) and (19), $k_1$ and $k_2$ are calibration constants dependant on the distance between the transducers. In addition, $k_1$ is dependent on the cross-sectional area of the channel and the distribution of the flow across it. The ultrasound measurements are performed fast, typically in a tenth of a millisecond, and therefore gives essentially instantaneous values for $\Phi_{actual}$ and $c_{actual}$. The subscript "actual" indicates that the flow and the sound velocity values obtained represent the flow and sound velocity at the present state of the gas, that is, the present pressure and temperature.

The velocity of sound in the gas depends on the molecular weight (M) and the absolute temperature (T) according to equation (20)

$$c^2 = \gamma \frac{R_M}{M} T \quad (20)$$

where $\gamma$ is the quotient of the specific heat capacities at constant pressure and constant volume, respectively ($C_p/C_v$), $R_M$ is the universal gas constant ($R_M$=8.3143 J/mol K), M is the mean molecular weight of the gas mixture (expressed as kg/mol), and T is the absolute temperature (expressed as Kelvin).

The quotient $\gamma$=1.40 for two-atomic gases at temperatures up to approximately 400 K.

The volumetric flow can be used to calculate a reference state according to the following: The mass flow through the ultrasound sensor can be expressed at a given state of the gas $\{p,T\}$, or at a reference state, as the volumetric flow multiplied by the density of the gas. That is:

$$\text{massflow} = \Phi_{actual} \rho_{actual} = \Phi_{ref} \rho_{ref} \quad (21)$$

$\Phi_{ref}$ is the volumetric flow at a (theoretical) reference state [m$^3$/s]

$\rho_{ref}$ is the density of the gas at the reference state [kg/m$^3$]

$\Phi_{actual}$ is the volumetric flow at the current state [m$^3$/s]

$\rho_{actual}$ is the density of the gas at the current state [kg/m$^3$]

Thus, this equation can be seen as a definition of the volumetric flow at the theoretical reference state.

The density, $\rho$, is determined from the ideal gas law:

$$\frac{p}{\rho} = \frac{R_M}{M} T \quad (22)$$

Substituted in equation (20) this yields (after eliminating the gas constant $R_M$ and the molecular weight M):

$$\Phi_{ref} \frac{p_{ref}}{T_{ref}} = \Phi_{actual} \frac{p_{actual}}{T_{actual}} \quad (23)$$

Equation (23) may be used to calculate the flow in a reference state defined by the selected pair $\{p_{ref}, T_{ref}\}$, based on the volumetric flow for the current state.

According to the invention an instantaneous value for the following expression is calculated:

$$W(t) = \Phi_{actual}(t) \frac{\gamma_0}{c_{actual}^2(t)} p_{actual}(t) \quad (24)$$

Thus, the current values of the volume flow and the sound velocity, $\Phi_{actual}$ and $c_{actual}$, are obtained from the ultrasound sensor, while the current pressure $p_{actual}$ is obtained from a separate pressure sensor. $\gamma_0$ is a constant factor.

Substituting (20) in (24) yields:

$$W(t) = \Phi_{actual}(t) \frac{\gamma_0}{\gamma(t)} \frac{M(t)}{R_M} \frac{p_{actual}(t)}{T_{actual}(t)} \quad (25)$$

By comparison with equation (23) equation (25) can be rewritten as $$W(t) = \frac{\gamma_0}{\gamma(t)} \Phi_{ref}(t) \frac{M(t)}{R_M} \frac{p_{ref}(t)}{T_{ref}(t)} \quad (26)$$

using the ideal gas law (22), equation (26) may be rewritten as $$W(t) = \frac{\gamma_0}{\gamma(t)} \Phi_{ref}(t) \rho_{ref}(t) \quad (27)$$

This means that if the constant $\gamma_0$ has been selected in such a way that $\gamma_0$ is a good approximation of $\gamma(t)$ the expression W(t) can be interpreted as the instantaneous mass flow through the ultrasound sensor (see equation 21). If $\gamma_0$ is not absolutely correct the expression will still yield a value that is proportional to the mass flow as long as $\gamma(t)$ is substantially constant.

In summary, by instantaneously calculating the following expression based on measurement data from the ultrasound sensor and the pressure sensor, $\{\Phi_{actual}, c_{actual}\}$ and $\{p_{actual}\}$, respectively:

$$W(t) = \Phi_{actual}(t) \frac{\gamma_0}{c_{actual}^2(t)} p_{actual}(t) \tag{28}$$

the instantaneous mass flow through the sensor can be obtained, provided that the factor $\gamma_0$ is selected correctly. This is valid as long as $\gamma(t)$ is substantially constant, which is known to be the case for mixtures of two-atomic gases at moderate temperatures.

As can be seen from Eq. (27), if $\gamma_0/\gamma(t)=1$, $W(t)$ is equal to the mass flow. Thus, if $\gamma_0/\gamma(t)=1$, the mass flow can be expressed as in Eq. (28).

Thus, the method according to the present invention can be summarized as in FIG. 7:

Step S11: Obtain the time of flight signals for the upstream and downstream

Step S12: Calculate the instantaneous volumetric flow and sound velocity for the gas (equations (18) and (29))

Step S13: measure the pressure in the gas flow.

Step S14: calculate a relationship between the actual volumetric flow, the actual sound velocity, the actual pressure and a constant $\gamma_0$ according to equation (28), which can be interpreted as the instantaneous mass flow through the ultrasonic sensor.

As will be understood, step S13 can be performed at any point in the procedure before step S14. In case the volumetric flow must be obtained by a separate sensor, which may be any kind of sensor known in the art, the time-of-flight signals may be obtained in a simplified way. Instead of obtaining the time-of-flight signal in both directions, one time-of-flight signal tof may be obtained using one or two ultrasonic transducers arranged orthogonally to the gas flow. In this case, the sound velocity is calculated according to the equation cactual=2k2/tof, a small modification of equation (19).

Based on the measured mass flow and the measured volumetric flow a density of the gas can be determined. The density at a particular point in time can be determined based on the quotient of the instantaneous mass flow and the instantaneous volumetric flow at the given time, as defined by Equation (29).

$$\rho(t) = \frac{\dot{m}(t)}{\dot{V}(t)} \tag{29}$$

Alternatively, the mean density can be determined as the quotient between a total mass and a total volume flowing through the tube during a certain period of time, for example, during one breath, as expressed in Equation (30).

$$\rho_{Cycle} = \frac{m_{Cycle}}{V_{Cycle}} \tag{30}$$

As explained in the introduction, the functional residual capacity of a person is the volume of the lung after expiration at normal pressure. End-expiratory lung volume (EELV) is defined as the volume of gas that remains in the respiratory passages of a patient that is being mechanically ventilated, at the end of a normal expiration. In the case of an elevated positive end expiratory pressure (PEEP), that is, if the end expiratory pressure is higher than the normal pressure, the end expiratory lung volume will be greater than the functional residual capacity.

Although modifications and changes may be suggested by those skilled in the art, it is the intention of the inventors to embody within the patent warranted heron all changes and modifications as reasonably and properly come within the scope of their contribution to the art.

We claim as our invention:

1. A ventilator for ventilation of a patient, comprising an inhalation gas circuit that provides breathing air comprising a mixture of N2 and O2 to the patient and an exhalation gas circuit that receives exhaled air from the patient, and a gas outlet for said exhaled air, and a control unit configured to calculate the end expiratory lung volume, EELV, of a patient being ventilated by the ventilator, based on the expired volume per breathing cycle, and a composition measuring unit configured to obtain a measurement of a quantity that varies linearly with the N2/O2 composition in the expired gas, said measuring unit being arranged near the gas outlet, the control unit being configured to determine the change in the N2/O2 composition in the expired gas between a first point in time ($t_1$) at which the N2/O2 composition of the breathing gas is changed from a first fixed composition to a second fixed composition, and a second point in time ($t_2$) at which the N2/O2 composition of the expired gas in at least two subsequent breaths is substantially stable, and said control unit being further configured to calculate, said EELV based on the measurement of the quantity that varies linearly with the N2/O2 composition in the expired gas, and the change in the N2/O2 composition exhaled and the total gas volume, for each breath between the first and the second points in time $t_1$ and $t_2$.

2. A ventilator according to claim 1, wherein the control unit is configured to calculate the end expiratory lung volume, EELV, according to $$EELV = \frac{\sum_{n=1}^{N} VCe_n \cdot (x_n - x_{after})}{x_{before} - x_{after}} - V_{system}$$

where $VCe_n$ is the volume of expired gas at breath number n, x is the quantity that varies linearly with the expired N2/O2 composition, $x_n$ is the value of the quantity at breath number n in each breath between the first and second points in time, $x_{before}$ is the value of the quantity before the first point in time and, $x_{after}$ is the value of the quantity at or just after the second point in time.

3. A ventilator according to claim 1, wherein the control unit is arranged to calculate the end expiratory lung volume, EELV, according to $$EELV = \frac{\sum_{n=1}^{N} VCe_n \cdot (O2mix_n - O2mix_{after})}{O2mix_{before} - O2mix_{after}} - V_{system}$$

where
- VCe$_n$ is the volume of expired gas at breath number n,
- O2mix$_n$ is the level of O$_2$ in the expired gas at breath number n between the first and second points in time,
- O2mix$_{after}$ is the level of O$_2$ in the expired gas at a breath just after the second point in time and
- O2mix$_{before}$ is the level of O2 in the expired gas before the first point in time.

4. A ventilator according to claim 1, wherein the control unit is configured to calculate the EELV according to $$EELV = \frac{\sum_{n=1}^{N} VCe_n \cdot (\rho_n - \rho_{after})}{\rho_{before} - \rho_{after}} - V_{system}$$

where
- $\rho_n$ is the density of the gas at breath number n between the first and second points in time,
- $\rho_{before}$ is the density of the gas at the first point in time, and
- $\rho_{after}$ is the density of the gas at or just after the second point in time.

5. A ventilator according to claim 4, wherein the control unit is configured to correct the values $\rho_n$, $\rho_{before}$ and $\rho_{after}$ for temperature before calculating the EELV, to eliminate the risk of a temperature induced drift.

6. A ventilator according to claim 1, wherein the control unit is configured to control the O2 level in the breathing gas supplied from the ventilator to the patient to change the O2 level in the breathing gas at the first point in time.

7. A ventilator according to claim 1, further comprising measuring unit that measures the volume flow of expired gas, said measuring unit being arranged near the gas outlet.

8. A ventilator according to claim 1, wherein the composition measuring unit comprises at least one ultrasonic sensor which is also used to measure both the volumetric flow and mass flow of the gas.

9. A control unit for a ventilator, said control unit being configured to calculate the end expiratory lung volume, EELV, of a patient being ventilated by the ventilator, based on the expired volume per breathing cycle, the change in N2/O2 composition in the expired gas between a first point in time (t$_1$) at which the N2/O2 composition of the breathing gas is changed from a first fixed composition to a second fixed composition, and a second point in time (t$_2$) at which the N2/O2 composition of the expired gas in at least two subsequent breaths is substantially stable, obtain a measurement of a quantity that varies linearly with the N2/O2 composition in the expired gas, said control unit being further configured to calculate, said EELV based on the measurement of the quantity that varies linearly with the N2/O2 composition in the expired gas, and the change in the N2/O2 composition exhaled and the total gas volume, for each breath between the first and the second points in time t$_1$ and t$_2$.

10. A control unit according to claim 9, wherein the control unit is configured to calculate the end expiratory lung volume, EELV, according to $$EELV = \frac{\sum_{n=1}^{N} VCe_n \cdot (x_n - x_{after})}{x_{before} - x_{after}} - V_{system}$$

where
- VCe$_n$ is the volume of expired gas at breath number n,
- x is a quantity that varies linearly with the expired N2/O2 composition, and
- x$_n$ is the value of the quantity at breath number n in each breath between the first and second points in time,
- x$_{before}$ is the value of the quantity at the first point in time, and
- x$_{after}$ is the value of the quantity at or just after the second point in time.

11. A control unit according to claim 9 configured to calculate the end expiratory lung volume, EELV, according to $$EELV = \frac{\sum_{n=1}^{N} VCe_n \cdot (O2mix_n - O2mix_{after})}{O2mix_{before} - O2mix_{after}} - V_{system}$$

where
- VCe$_n$ is the volume of expired gas at breath number n between the first and second points in time,
- O2mix$_n$ is the level of O$_2$ in the expired gas at breath number n between the first and second points in time,
- O2mix$_{after}$ is the level of O$_2$ in the expired gas at a breath just after the second point in time, and
- O2mix$_{before}$ is the level of O2 in the expired gas before the first point in time.

12. A control unit according to claim 9, configured to calculate the EELV based on flow data received from an ultrasonic sensor.

13. A control unit according to claim 12, configured to calculate the EELV according to $$EELV = \frac{\sum_{n=1}^{N} VCe_n \cdot (\rho_n - \rho_{after})}{\rho_{before} - \rho_{after}} - V_{system}$$

where
- $\rho_n$ is the density of the gas at breath number n between the first and second points in time,
- $\rho_{before}$ is the density of the gas at the first point in time, and
- $\rho_{after}$ is the density of the gas at or just after the second point in time.

14. A control unit according to claim 13, configured to correct the values $\rho_n$, $\rho_{before}$ and $\rho_{after}$ for temperature before calculating the EELV, to eliminate the risk of a temperature induced drift.

15. A control unit according to claim 13 further configured to control the O2 level in the breathing gas supplied from the ventilator to the patient to change the O2 level in the breathing gas at the first point in time.

16. A method of determining an end-expiratory lung volume, EELV, for a mechanically ventilated patient, where a breathing gas is provided to the patient through an inspiratory tube and removed from the patient through an expiratory tube, said method comprising the steps:
- providing a breathing gas comprising a first fixed N2/O2 gas composition to the patient at least until the N2/O2 gas composition in air expired from the patient is constant;
- changing, at least once, at a determined point in time (t$_1$), the N2/O2 gas composition to a second fixed composition in the breathing gas;

measuring the change in N2/O2 gas composition exhaled by the patient for each breath until a point in time ($t_2$) at which the level of expired $O_2$ in at least two subsequent breaths is substantially stable, said measurement being made downstream of the expiratory tube;

making a measurement of a quantity that varies linearly with the N2/O2 composition in the expired gas;

determining the total gas volume of each breath; and in a processor, determining the EELV of the patient's lungs based on the measurement of the quantity that varies linearly with the N2/O2 composition in the expired gas, and based on the change in the N2/O2 gas composition $O_2$ level between the first and second points in time, for each breath between the first and the second points in time $t_1$ and $t_2$.

17. A method according to claim 16, comprising changing the N2/O2 composition by reducing the level of O2.

18. A method according to claim 16, comprising changing the N2/O2 composition by increasing the level of O2.

19. A method according to claim 16 comprising changing the level of O2 by changing the level of O2 by a unit of between 5% and 35% of the total volume.

20. A method according to claim 19 comprising determining the total gas volume of each breath using a volume sensor downstream of the expiratory tube.

21. A method according to claim 16 comprising determining EELV according to the following equation:

$$EELV = \frac{\sum_{n=1}^{N} VCe_n \cdot (x_n - x_{after})}{x_{before} - x_{after}} - V_{system}$$

where $VCe_n$ is the volume of expired gas at breath number n, x is a quantity that varies linearly with the expired N2/O2 composition, and $x_n$ is the value of the quantity at breath number n in each breath between the first and second points in time, $x_{before}$ is the value of the quantity at the first point in time, and $x_{after}$ is the value of the quantity at or just after the second point in time.

22. A method according to claim 16 comprising determining EELV according to the following equation:

$$EELV = \frac{\sum_{n=1}^{N} VCe_n \cdot (O2mix_n - O2mix_{after})}{O2mix_{before} - O2mix_{after}} - V_{system}, \text{ where}$$

$VCe_n$ is the volume of expired gas at breath number n, $O2mix_{before}$ is the level of O2 in the expired gas at the first point in time, $O2mix_n$ is the level of O2 in the expired gas at breath number n between the first and second points in time, and $O2mix_{after}$ is the level of $O_2$ in the expired gas at a breath just after the second point in time.

23. A method according to claim 16 comprising determining EELV according to the following equation:

$$EELV = \frac{\sum_{n=1}^{N} VCe_n \cdot (\rho_n - \rho_{after})}{\rho_{before} - \rho_{after}} - V_{system}, \text{ where}$$

$\rho_n$ is the density of the gas at breath number n between the first and second points in time, $\rho_{before}$ the density of the gas at the first point in time, and $\rho_{after}$ is the density of the gas at or just after the second point in time.

24. A method according to claim 23, further comprising the step of correcting the values $\rho_n$, $\rho_{before}$ and $\rho_{after}$ for temperature before calculating the EELV, to eliminate the risk of a temperature induced drift.

* * * * *